(12) United States Patent
Mizutani et al.

(10) Patent No.: US 6,475,200 B2
(45) Date of Patent: Nov. 5, 2002

(54) ABSORBENT ARTICLE

(75) Inventors: Satoshi Mizutani, Kagawa (JP); Tatsuya Tamura, Kagawa (JP); Yuuki Noda, Kagawa (JP)

(73) Assignee: Uni-Charm Corporation, Ehime (JP)

(*) Notice: Subject to any disclaimer, the term of this patent is extended or adjusted under 35 U.S.C. 154(b) by 0 days.

(21) Appl. No.: 09/803,806

(22) Filed: Mar. 12, 2001

(65) Prior Publication Data

US 2001/0021838 A1 Sep. 13, 2001

(30) Foreign Application Priority Data

Mar. 13, 2000 (JP) ........................................ 2000-068352

(51) Int. Cl.$^7$ ................................................ A61F 13/15
(52) U.S. Cl. ............................ 604/385.01; 604/385.04; 604/385.28
(58) Field of Search ....................... 604/385.04, 385.28, 604/385.01

(56) References Cited

U.S. PATENT DOCUMENTS

| | | | |
|---|---|---|---|
| 4,695,278 A | 9/1987 | Lawson | ........................ 604/385 |
| 5,181,563 A | 1/1993 | Amaral | ..................... 604/385.2 |
| 5,518,801 A | 5/1996 | Chappell et al. | ............. 428/152 |
| 5,810,800 A | 9/1998 | Hunter et al. | ............. 604/285.2 |
| 5,921,975 A | 7/1999 | Suzuki et al. | ............. 604/385.2 |

FOREIGN PATENT DOCUMENTS

| | | |
|---|---|---|
| EP | 0750894 | 1/1997 |
| EP | 1101476 | 5/2001 |
| WO | WO9508972 | 4/1995 |
| WO | WO9623471 | 8/1996 |

*Primary Examiner*—Rodney M. Lindsey
*Assistant Examiner*—Angela J Grayson
(74) *Attorney, Agent, or Firm*—Darby & Darby

(57) ABSTRACT

There is disclosed an absorbent article including: a main body; and leakage preventing side walls provided on two sides of the main body to have root ends jointed to the surface of the liquid receiving side and to have free ends positioned apart therefrom. Each leakage preventing side wall includes: a nonwoven fabric of thermoplastic fibers; and an elastic member for exhibiting an elastic shrinking force in the longitudinal direction. The nonwoven fabric is provided with: at least two rigid regions having corrugations, ridges and valleys of which are individually extended in a direction from the root end to the free end and are repeated regularly in the longitudinal direction; and a rigid boundary portion in which the corrugations are discontinuous and which is extended in the longitudinal direction midway between the root end and the free end.

5 Claims, 9 Drawing Sheets

ABSORBENT ARTICLE

BACKGROUND OF THE INVENTION

1. Field of the Invention

The present invention relates mainly to an absorbent article for absorbing and retaining a liquid waste such as menstrual blood and, more particularly, to an absorbent article having leakage preventing side walls on the two widthwise sides of the liquid receiving side.

2. Related Art

In the prior art, there have been a variety of absorbent articles including a sanitary napkin, a urine absorbing pad and a disposable diaper. These absorbent articles are demanded, when worn, for absorbing the liquid waste reliably in liquid absorbing layers so that the liquid waste may not leak to the outside of the absorbent articles. For this purpose, there is an absorbent article which is provided on the surface of the liquid receiving side with leakage preventing side walls extending longitudinally on the two widthwise sides.

In the general structure of the leakage preventing side walls of the prior art, a longitudinally extending unstretchable hydrophobic sheet is jointed to the top sheet of the absorbent article, and an elastic member extending longitudinally of the absorbent article is jointed to the hydrophobic sheet. By the elastic shrinking force in the longitudinal direction of the elastic member, a curving force in the longitudinal direction is applied to the absorbent article, and the leakage preventing side walls are raised to the liquid receiving side of the absorbent article so that the menstrual blood or the like may be prevented from leaking sideways.

In the leakage preventing side walls in which longitudinally extending elastic members are attached to the unstretchable hydrophobic sheet, however, this hydrophobic sheet is irregularly wrinkled by the longitudinal elastic shrinking forces of the elastic members. If the unstretchable hydrophobic sheet thus has many irregular wrinkles in which the ridges and valleys are individually extended in the widthwise direction and are repeated in the longitudinal direction, the leakage preventing side walls acquire a high bending rigidity in the widthwise direction so that they become planar in the widthwise direction. Then, the leakage preventing side walls hardly follow the shape of the skin surface of a wearer so that the wearer feels a sense of discomfort. If a high external force acts on the portion where the bending rigidity in the widthwise direction is high, moreover, the leakage preventing side walls are collapsed in the widthwise direction so that they remain broken to fail to restore their original shapes. As a result, the contact of the leakage preventing side walls with the wearer's skin is easily deteriorated to cause a sideway leakage.

If the ridges and valleys of the irregular wrinkles are individually extended in the longitudinal direction and are repeated in the widthwise direction, or if the ridges and valleys of the wrinkles are individually extended obliquely with respect to the longitudinal and widthwise directions, on the other hand, the hydrophobic sheet being subjected to the elastic shrinking force is rounded or irregularly folded on the liquid receiving side of the absorbent article being worn. Then, the contact between the leakage preventing side walls and the wearer's skin becomes unstable to form a clearance easily between the leakage preventing side walls and the skin. In this case, the sideway leakage cannot be completely prevented.

SUMMARY OF THE INVENTION

The invention has an object to provide an absorbent article which is enabled to curve the leakage preventing side walls easily in the widthwise direction to form a three-dimensional stereoscopic shape according to the shape of the skin of a wearer, by forming regions having a high bending rigidity in the widthwise direction, in advance in the leakage preventing side walls to be subjected to a shrinking force by elastic members and by making a rigidity difference in the widthwise direction.

According to an aspect of the invention, there is provided an absorbent article comprising: a main body including a support sheet, a liquid absorbing layer laid on the support sheet, and a liquid-permeable sheet provided on a liquid receiving side of the main body and covering the liquid absorbing layer; and leakage preventing side walls provided on two sides of the main body lying opposite one another in the widthwise direction and extending in the longitudinal direction, to have root ends jointed to the surface of the liquid receiving side and to have free ends positioned apart from the surface of the liquid receiving side, wherein each leakage preventing side wall includes: a nonwoven fabric comprising thermoplastic fibers; and an elastic member for exhibiting an elastic shrinking force in the longitudinal direction, wherein the nonwoven fabric is provided with: at least two rigid regions having corrugations, ridges and valleys of which are individually extended in a direction from the root end to the free end of the leakage preventing side wall and are repeated regularly in the longitudinal direction; and a rigid boundary portion in which the corrugations are discontinuous and which is extended in the longitudinal direction midway between the root end and the free end of the leakage preventing side wall.

In the invention, the nonwoven fabric making the leakage preventing side wall contains the thermoplastic fibers and is pressure/heat-shaped to form the regular corrugations. The ridges and valleys of the corrugations are individually extended in the widthwise direction on the leakage preventing side wall so that the rigid regions having the corrugations are higher in the widthwise bending rigidity. Therefore, the rigid regions are not extremely bent by an external force but can keep the extended state in the widthwise direction. Since the rigid boundary portion is formed midway between the root end and the free end, however, the leakage preventing side wall can be easily bent and deformed in the widthwise direction across the rigid boundary portion. Therefore, the leakage preventing side walls can be easily curved in the widthwise direction according to the curved shape of the skin of the wearer so that they can take the three-dimensional stereoscopic shapes easily. As a result, the leakage preventing side walls can come into close contact with the skin to prevent the sideway leakage effectively.

In the invention, since the leakage preventing side walls are made of the nonwoven fabric, they are sufficiently soft. If the corrugations are given a pitch as fine as 0.3 to 1.5 mm or more preferably about 0.5 to 1.0 mm, moreover, the leakage preventing side walls come into soft abutment against the skin so that the wearer hardly feels the sense of discomfort.

For example, midway between the root end and the free end of the leakage preventing side wall, there is formed a band-shaped region in which the nonwoven fabric is not corrugated or is corrugated lower than the corrugations and which is extended in the longitudinal direction, and a boundary line between the corrugations and the band-shaped region is the rigid boundary portion.

The leakage preventing side wall may have the elastic member attached to the free end but not to the vicinity of the rigid boundary portion.

In an alternative, the leakage preventing side wall may have the elastic member attached to the vicinity of the rigid boundary portion but not to the free end.

In another alternative, the leakage preventing side wall may have two elastic members attached to the free end and the vicinity of the rigid boundary portion, respectively. In this case, it is preferred that the elastic member at the free end has a higher elastic shrinking force than that of the elastic member in the vicinity of the rigid boundary portion.

The leakage preventing side wall may be made to have at least two sheet portions either by folding a single nonwoven fabric, as extending from the root end, back at the free end to the root end, or by jointing a plurality of nonwoven fabrics, as individually extending from the root end, to one another in the longitudinal direction at the free end or another region, and the rigid regions and the rigid boundary portion may be formed in the individual sheet portions at the same positions of the leakage preventing side wall.

Since the leakage preventing side wall is made of the two sheet portions of the nonwoven fabric, its leakage preventing effect as well as its rigidity in the rigid regions can be enhanced, and the leakage preventing side wall can be softly deformed across the rigid boundary portion.

DESCRIPTION OF THE PREFERRED EMBODIMENTS

Figure 1:
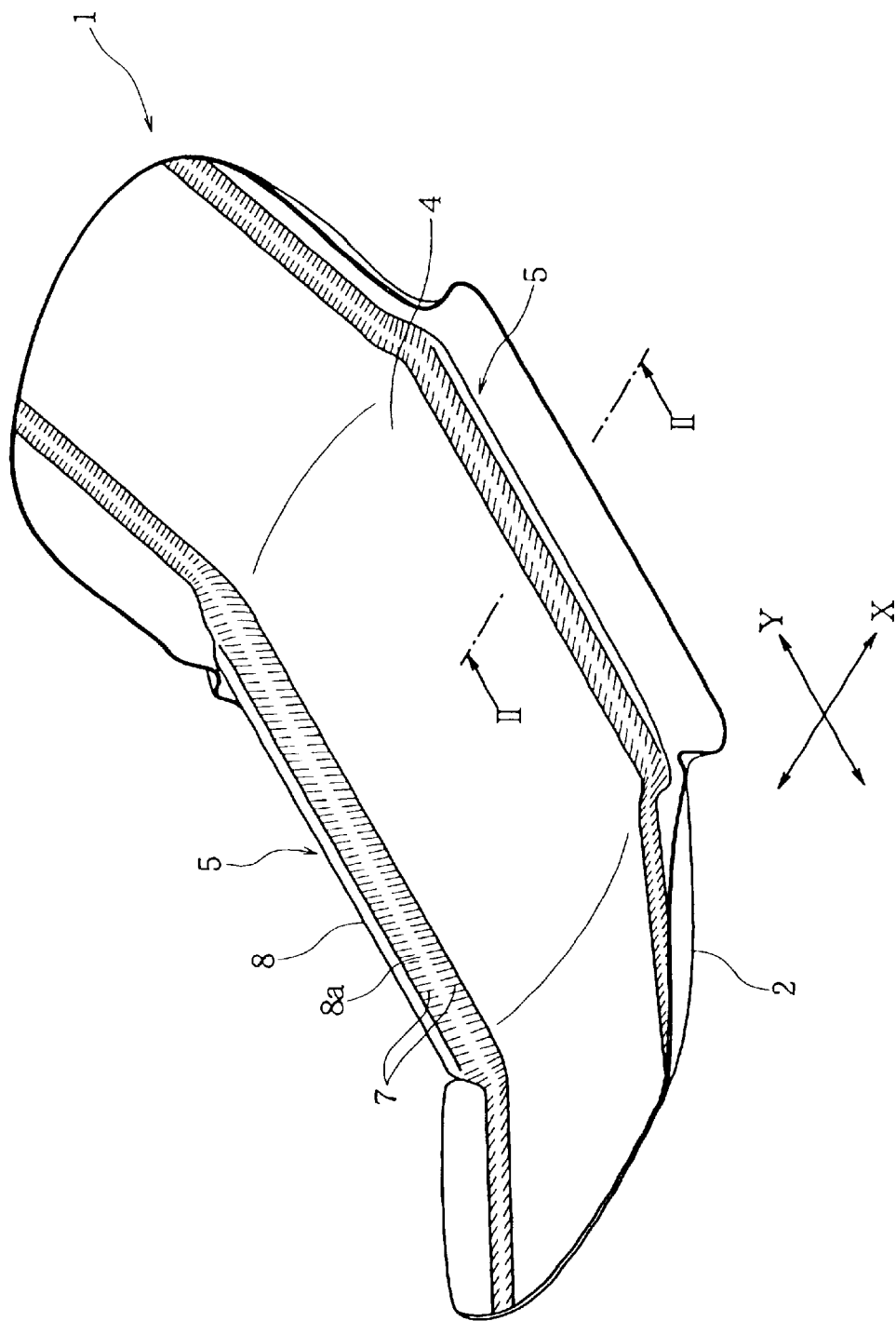
FIG. 1 is a perspective view showing a sanitary napkin as an absorbent article according to a first embodiment of the invention.
Figure 2:
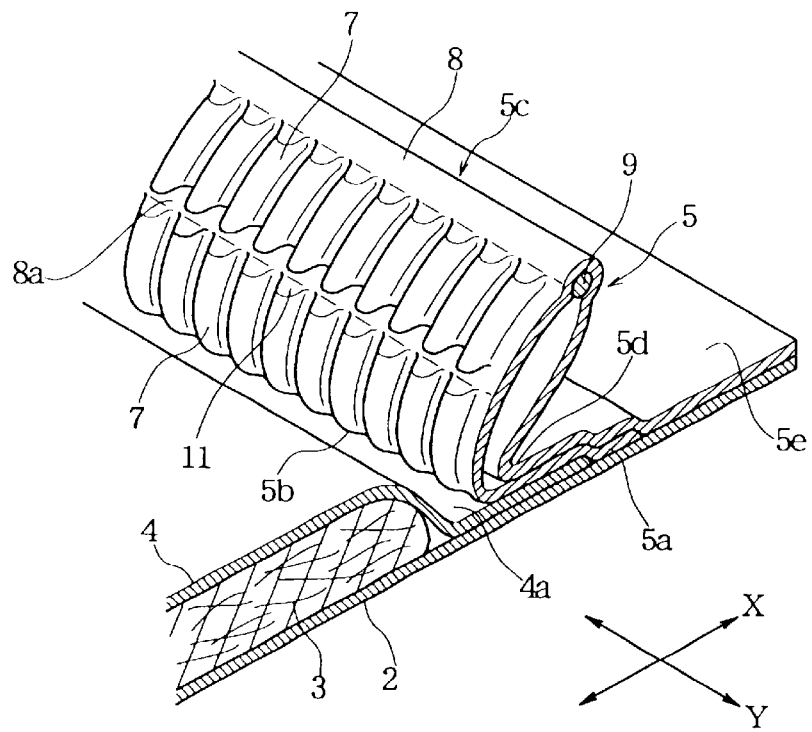
FIG. 2 is a perspective view showing a portion of the sanitary napkin shown in FIG. 1 and including a section taken along line II—II.
Figure 3:
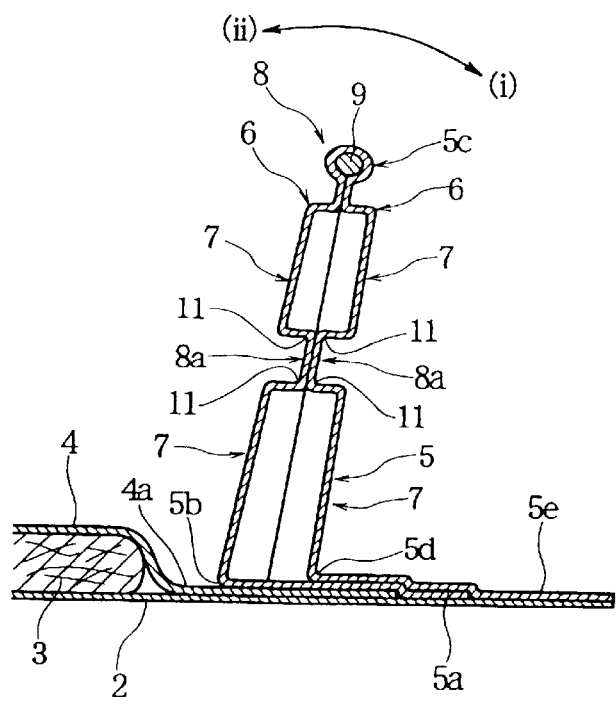
FIG. 3 is a section of the sanitary napkin shown in FIG. 2.
Figure 8:
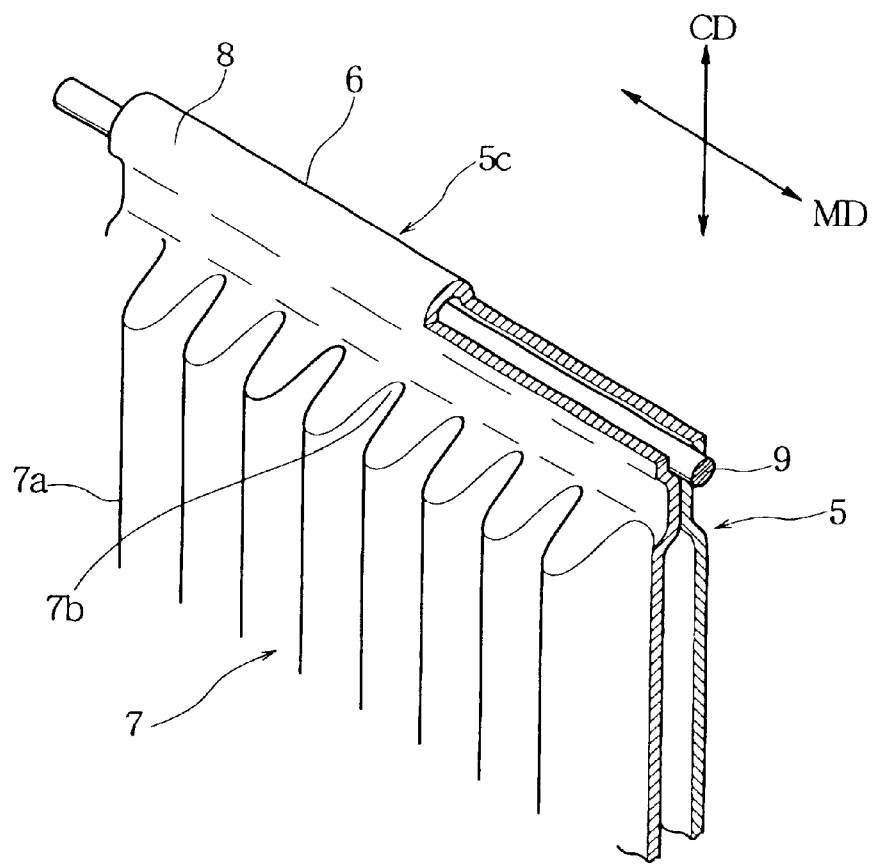
FIG. 8 is an enlarged perspective view showing a free end portion of a side wall sheet.

The invention will be described with reference to the accompanying drawings. FIG. 1 is a perspective view showing a sanitary napkin as an absorbent article according to a first embodiment of the invention and taken from a liquid receiving side; FIG. 2 is a perspective view showing a portion and including a section taken along line II—II of FIG. 1; FIG. 3 is a section of a leakage preventing side wall shown in FIG. 2; and FIG. 8 is an enlarged perspective view showing a portion of a free end portion of the side wall sheet.

A sanitary napkin 1, as shown in FIGS. 1, 2 and 3, is constructed to have a main body including: a support sheet 2 for confronting an external wear such as an underwear; a liquid absorbing layer 3 positioned on the side of the wearer for absorbing the liquid waste; and a liquid-permeable sheet 4 for covering the surface of the liquid receiving side of the liquid absorbing layer 3. Side end portions 4a of the liquid-permeable sheet 4 lying opposite one another in the widthwise direction (or a direction X) are jointed onto the surface of the support sheet 2 on two sides of the liquid absorbing layer 3.

On the two side portions of the sanitary napkin 1 lying opposite one another in the widthwise direction (or the direction X), there are provided a pair of leakage preventing side walls 5 and 5 which extend in the longitudinal direction (or a direction Y). In this embodiment, the individual leakage preventing side walls 5 and 5 are made of one side wall sheet 6.

The side wall sheet 6 is made of a hydrophobic nonwoven fabric. This sidewall sheet 6 is jointed at its one end portion 5a onto the support sheet 2 and the side end portion 4a of the liquid-permeable sheet 4. The side wall sheet 6 is extended away from the support sheet 2 to form one root end 5b of the side wall 5 on the side end portion 4a of the liquid-permeable sheet 4 and is then folded back to form a free end 5c of the side wall 5. Moreover, the side wall sheet 6 is returned to the support sheet 2 and is so jointed at its other end portion 5e to the upper face of the support sheet 2 that another root end 5d of the side wall 5 is formed and jointed onto the side end portion 4a of the liquid-permeable sheet 4. Therefore, the leakage preventing side wall 5 has a double structure in which the two folded portions (or inner and outer sheet portions) of the side wall sheet (of the nonwoven fabric) 6 are overlaid in the widthwise direction (or the direction X).

As shown in FIG. 8, the side wall sheet 6 is formed with corrugations 7. These corrugations 7 have ridges 7a and valleys 7b repeated in the longitudinal direction (or the direction Y). The ridges 7a and the valleys 7b are individually extended in the direction from the root ends 5b and 5d to the free end 5c of the leakage preventing side wall 5.

As shown in FIGS. 2, 3 and 8, moreover, the side wall sheet 6 is formed with band-shaped regions 8 and 8a, which are extended in the longitudinal direction (or the direction Y). In the band-shaped regions 8 and 8a, the side wall sheet 6 is never corrugated or is corrugated lower than the aforementioned corrugations to have a smooth or relatively smooth surface. Alternatively, the band-shaped regions 8 and 8a may be formed by crushing the corrugations 7 completely or to some degree. The side wall sheet 6 is folded back at the band-shaped portion 8 to form the free end 5c of the leakage preventing side wall 5. To this free end 5c, moreover, there is internally jointed an elastic member 9.

On the other hand, the band-shaped regions 8a are so formed on the leakage preventing side wall 5 midway between the root ends 5b and 5d and the free end 5c as to extend continuously in the longitudinal direction. However, these band-shaped regions 8a may be extended intermittently at an interval in the longitudinal direction. As shown in FIG. 3, the corrugations 7 and the band-shaped regions 8a are formed at substantially equal height positions individually on the inner and outer sheet portions of the side wall sheet 6 (i.e., the two folded portions of the side wall sheet 6 folded back at the free end 5c) composing the leakage preventing side wall 5.

Here, at the band-shaped regions 8a, the inner and outer sheet portions of the side wall sheet 6 may contact each other, as shown in FIG. 3, or may not contact each other, as shown in FIG. 2.

In this leakage preventing side wall 5, the regions where the numerous corrugations 7 are regularly formed are rigid regions which have a higher bending rigidity in the direction from the root ends 5b and 5d to the free end 5c (in the widthwise direction or the direction X). On the other hand, the band-shaped region 8a is a lower rigid region which has a lower bending rigidity in the direction from the root ends to the free end, as compared with the aforementioned rigid regions having the corrugations 7. Moreover, a rigid boundary portion 11 is located on the boundary line between the rigid region having the corrugations 7 and the lower rigid region (or the band-shaped region 8). Where the leakage preventing side wall 5 is formed of the two folded portions of the side wall sheet 6, as shown in FIGS. 2 and 3, the rigid boundary portions 11 are preferably formed at the same positions of the two folded portions of the side wall sheet 6.

The side wall sheet 6 is made of a nonwoven fabric having no or little stretchability by itself, but is corrugated at 7, so that it is allowed to exhibit a little elastic shrinking force in the longitudinal direction (or the direction Y) by the extension and shrinkage of the corrugations 7. Since the free end 5c is provided with the elastic member 9, on the other hand, a strong elastic shrinking force acts in the longitudinal direction (or the direction Y) upon the free end 5c.

At the two end portions of the sanitary napkin 1 lying opposite one another in the longitudinal direction (or the direction Y), as shown in FIG. 1, the leakage preventing side walls 5 are jointed to the surface of the liquid receiving side of the main body while falling down outwardly in the widthwise direction. By the elastic shrinking force in the direction Y of the elastic members 9, therefore, the sanitary napkin 1 is so curved that its liquid receiving side is recessed in the longitudinal direction (or the direction Y), and the leakage preventing side walls 5 are raised at their free ends 5c apart from the support sheet 2. Here in the embodiment shown in FIGS. 2 and 3, the leakage preventing side walls 5 and 5 are so obliquely raised that the free ends 5c are directed outwardly in the widthwise direction with respect to the root ends 5b and 5d.

In the side wall sheets 6 forming the leakage preventing side walls 5 of this sanitary napkin 1, the portions having the corrugations 7 are the rigid regions where the bending rigidity becomes higher in the direction from the root ends 5b and 5d to the free end 5c, but the lower rigid regions, i.e., the band-shaped regions 8a and the rigid boundary portions 11 are formed in the midway regions between the root ends 5b and 5d and the free ends 5c. Therefore, the leakage preventing side walls 5 are easily folded and deformed in the directions (i) and (ii) in FIG. 3 across the band-shaped regions 8a or the rigid boundary portions 11.

On the other hand, the leakage preventing side walls 5 can be made soft and deformable in the longitudinal direction (or the direction Y) in which the corrugations 7 are arrayed. Therefore, the leakage preventing side walls 5 can be freely deformed as a whole while following the three-dimensional stereoscopic shape according to the shape of the crotch of a wearer's body. In the rigid regions having the corrugations 7, moreover, the bending rigidity is so high as to apply a force to keep the planar shape. There is eliminated a disadvantage that the leakage preventing side walls 5 are irregularly folded or folded back to fail to restorations at the portions having the corrugations 7 other than the band-shaped regions 8a and the rigid boundary portions 11.

Therefore, the leakage preventing side walls 5 easily contact with the wearer's skin in accordance with the surface shape of the skin so that the clearance from the skin is hardly formed to enhance the sideway leakage preventing effect. In addition, since the side wall sheets 6 forming the leakage preventing side walls 5 are made of the nonwoven fabric, and the pitch of the corrugations 7 are as fine as no less than 0.3 mm and no more than 1.5 mm, preferably no less than 0.5 mm and no more than 1.0 mm, the leakage preventing side walls 5 softly contact with the skin. Moreover, the leakage preventing side walls 5 are easily deformable into the three-dimensional stereoscopic shape, as described above, so that the wearer hardly feels the sense of discomfort when the leakage preventing side walls come into abutment against the skin.

The menstrual blood, as received on the liquid receiving side of the sanitary napkin 1, is absorbed through the liquid-permeable sheet 4 by the liquid absorbing layer 3. When the menstrual blood is given to the inner sheet portion (i.e., the portion facing the side of the liquid absorbing layer 3) of the side wall sheet 6 of the leakage preventing side wall 5, it is guided on the surface of the side wall sheet 6 along the valleys 7b of the-corrugations 7 onto the liquid-permeable sheet 4. Here in the embodiment shown, the leakage preventing side wall 5 is jointed on the side end portion 4a, as extended sideway of the liquid absorbing layer 3, of the liquid-permeable sheet 4. As described hereinbefore, therefore, the menstrual blood having migrated over the surface of the side wall sheet 6 to the root end side is fed to the liquid-permeable sheet 4 so that it is easily led to the liquid absorbing layer 3. In an alternative, the leakage preventing side walls 5 may be given the structure in which they rise from the central portion, as located between the two side end portions 4a and 4a and covering the liquid absorbing layer 3, of the liquid-permeable sheet 4. With such a structure, also, the menstrual blood having migrated over the surface of the side wall sheet 6 can be easily absorbed through the liquid-permeable sheet 4 by the liquid absorbing layer 3.

Figure 9:
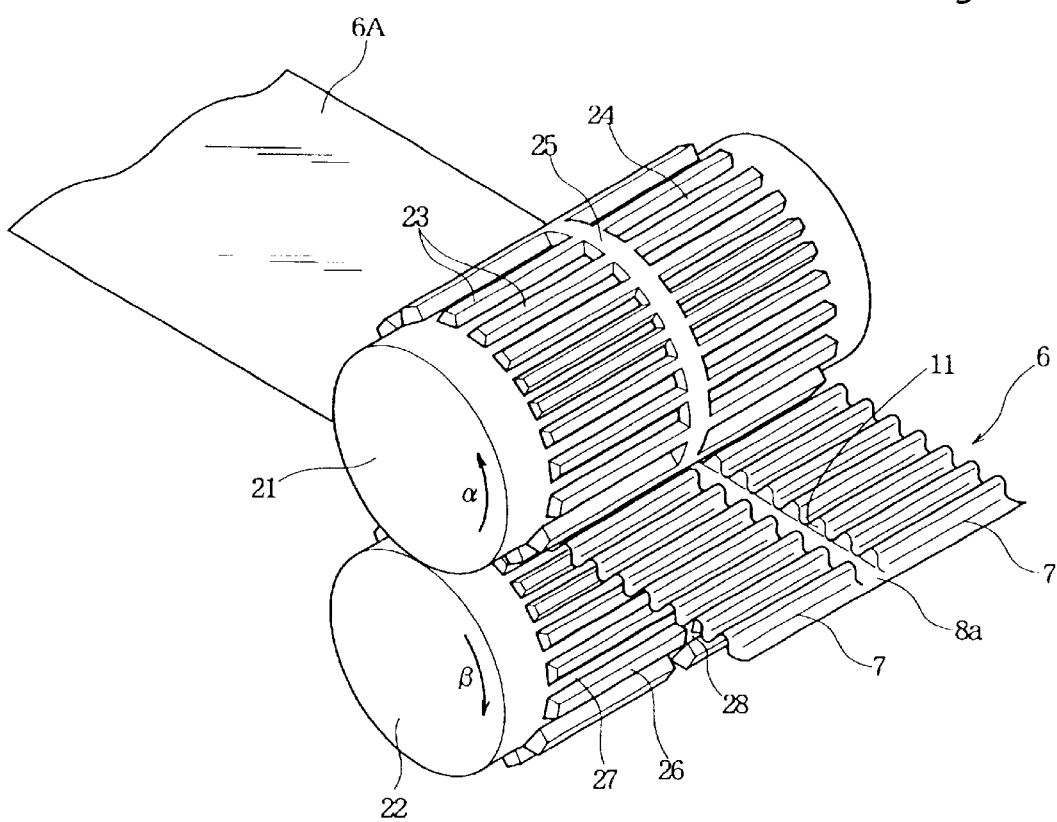
FIG. 9 is a perspective view of shaping rolls for forming the side wall sheet.

FIG. 9 is a view for explaining a heat-pressing step of forming the corrugations 7 and the band-shaped regions 8a (and the band-shaped regions 8) on the side wall sheet 6 and simultaneously forming the rigid boundary portions 11 in the boundary portion between the corrugations 7 and the band-shaped regions 8a. Here, FIG. 9 shows only one band-shaped region 8a, but a plurality of band-shaped regions could be simultaneously formed at a heat-pressing step similar to that of FIG. 9.

At this heat-pressing step, a nonwoven fabric such as a melt-blown nonwoven fabric formed of or containing thermoplastic fibers is heat-pressed by clamping it between shaping rolls 21 and 22. These shaping rolls 21 and 22 are turned in directions α and β while meshing with each other.

Figure 10A:
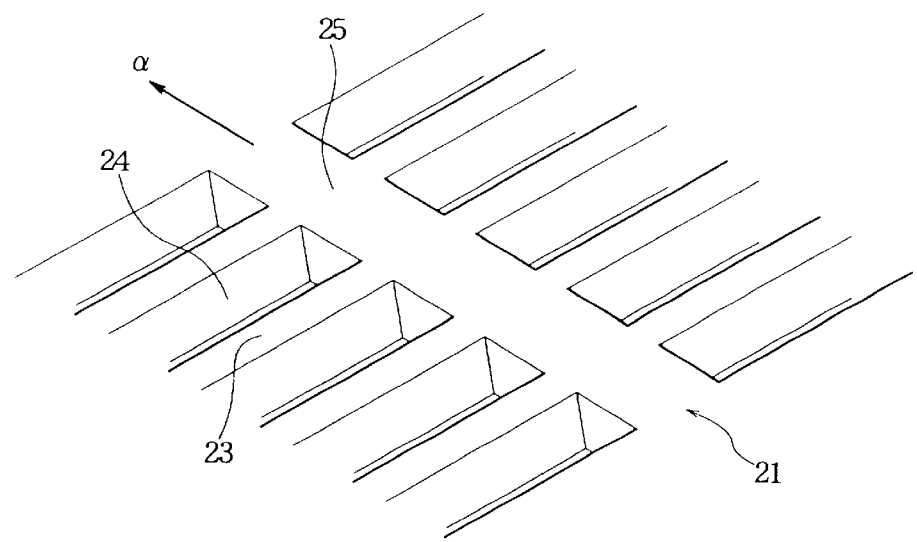
FIGS. 10A and 10B are developed perspective views of the shaping faces of the shaping rolls shown in FIG. 9.

The shaping roll 21 has a shaping face formed on its surface. FIG. 10A develops and shows the top plan view of the shaping face of the surface of the shaping roll 21. In the shaping face of the shaping roll 21, there are stripe embossed shaping ribs 23 and grooves 24 which are extended in the axial direction of the roll and repeated at a constant pitch in the turning direction (or the direction α). At the axial central portion of the shaping roll 21, there is formed a bulging circumference 25 which continues to the upper faces of the shaping ribs 23 and is extended continuously in the turning direction (or the direction α).

Figure 10B:
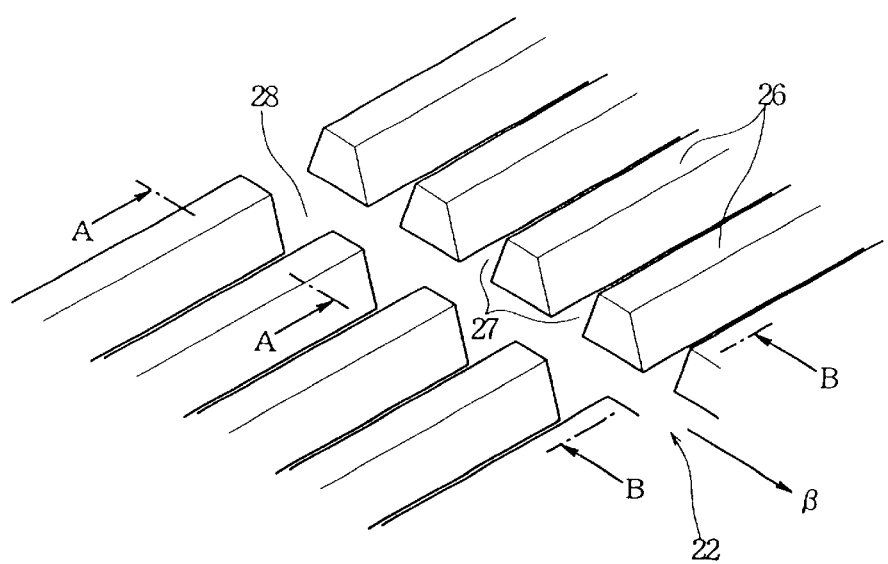

FIG. 10B develops and shows the shaping face of the surface of the other shaping roll 22. In the shaping face of the surface of the shaping roll 22, there are stripe embossed shaping ribs 26 and grooves 27 which are extended in the axial direction of the roll and repeated at a constant pitch in the turning direction (or the direction β). At the axial central portion of the shaping roll 22, there is formed a recessed circumference 28 which continues to the bottom portions of the grooves 27 and is extended continuously in the turning direction (or the direction β).

When the shaping rolls 21 and 22 come into meshing engagement, the shaping ribs 23 of the shaping roll 21 and the shaping ribs 26 of the shaping roll 22 mesh with each other such that the shaping ribs 23 enter the grooves 27 of the shaping roll 22 whereas the shaping ribs 26 enter the grooves 24 of the shaping roll 21. At this time, the bulging circumference 25 of the shaping roll 21 bites into the recessed circumference 28 of the shaping roll 22.

When a nonwoven fabric 6A is clamped between the shaping rolls 21 and 22 and is let off as the rolls turn, as shown in FIG. 9, the corrugations 7, the band-shaped region 8a and the rigid boundary portions 11 are simultaneously formed by the shaping faces of the shaping rolls 21 and 22, to thereby form the side wall sheet 6.

The side wall sheet 6 is made of a melt-blown nonwoven fabric, an air-through nonwoven fabric, a spun-bonded nonwoven fabric, a point-bonded nonwoven fabric, an air-laid nonwoven fabric or the like. However, the side wall sheet 6 may be made of a laminate material of the nonwoven fabric and a resin film.

These nonwoven fabrics 6A are made of the PE, PP or PET fibers, or composite synthetic fibers of the core-sheath type of the PE/PP or PE/PET or of the side-by-side type thereof.

Figure 11A:
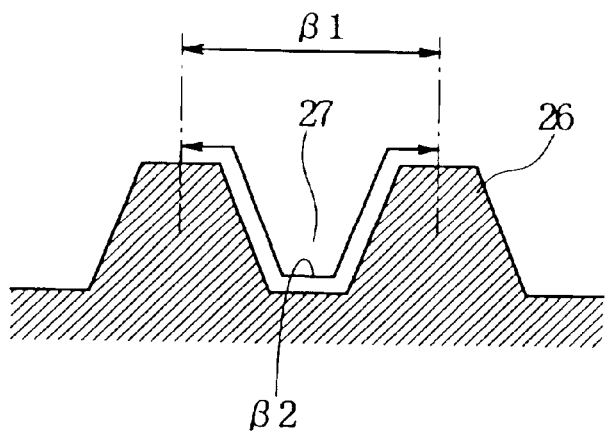
FIGS. 11A and 11B are enlarged sections taken along lines A—A and B—B of FIG. 10B.
Figure 11B:
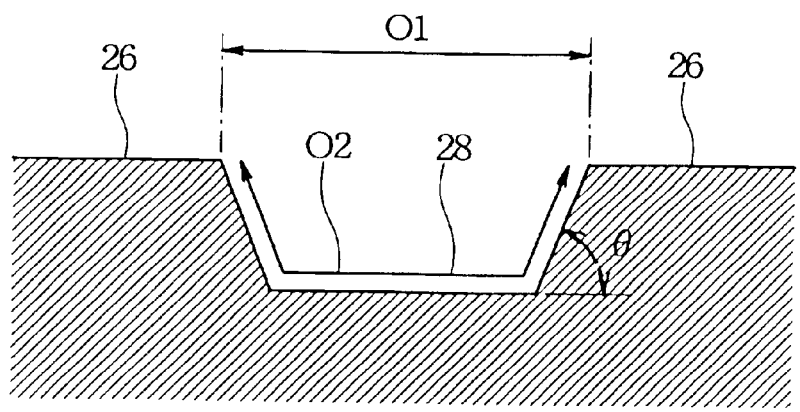

FIG. 11A is a section showing the shaping face of the shaping roll 22 and taken along line A—A of FIG. 10B, and FIG. 11B is a section taken along line B—B of FIG. 10B. The shaping faces of the shaping rolls 21 and 22 are preferably set to a temperature which is lower by 10° C. to 50° C., for example, than the melting point of the thermoplastic resin making the aforementioned nonwoven fabric 6A.

In FIG. 11A, the array pitch of the shaping ribs 26 in the turning direction (or the direction β) is indicated by β1, and the exceeding size extending through the shaping ribs 26 and the grooves 27 between the array pitch β1 is indicated by β2. When the nonwoven fabric 6A is clamped between the shaping rolls 21 and 22 and let off, the nonwoven fabric 6A is given a shaping distortion of $\{(\beta2-\beta1)/\beta1\}$. This shaping distortion at this time is set to a value smaller than the rupture elongation (or rupture distortion) in the let-off direction of the nonwoven fabric. As a result, the corrugations 7 are formed without rupture on the nonwoven fabric 6A.

If the distance, as taken in the roll axis direction, of the open end of the recessed circumference 28 is indicated by O1 and if the exceeding size, as adding the undulations in the widthwise direction, of the recessed circumference 28 is indicated by O2, as shown in FIG. 11B, the nonwoven fabric 6A is given a shaping distortion of $\{(O2-O1)/O1\}$ in the roll axis direction (or the widthwise direction of the nonwoven fabric 6A). This shaping distortion is set no more than the rupture elongation (or the ruptured distortion) in the width wise direction of the nonwoven fabric 6A. Then, the band-shaped region 8a, as extended in the let-off direction, is formed at the widthwise central portion of the nonwoven fabric 6A by the shaping rolls 21 and 22, and the rigid boundary portions 11 are formed at the boundary portions between the corrugations 7 and the band-shaped region 8a.

Here, in order to form the rigid boundary portions 11 by causing no rupture in the nonwoven fabric, the rising angle θ at the two widthwise side portions of the recessed circumference 28 is preferably at least 90 degrees and at most 135 degrees.

Figure 12:
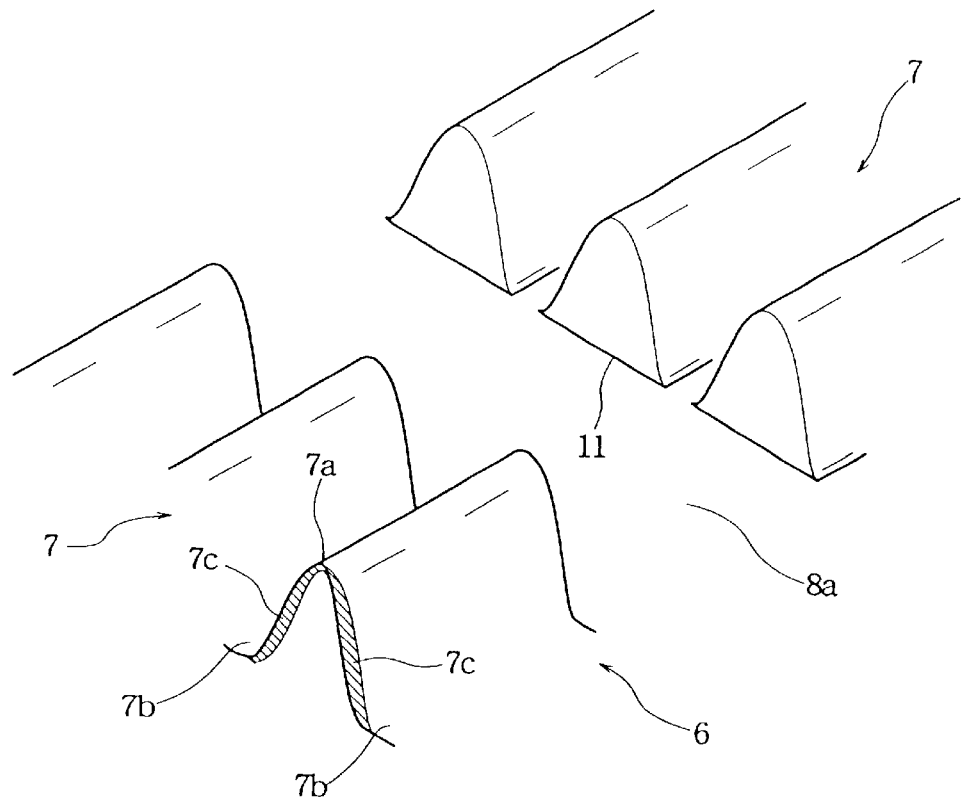
FIG. 12 is an enlarged perspective view of a portion of the side wall sheet which is provided with corrugations, a band-shaped region and rigid boundary portions.

FIG. 12 shows the portion, in which the band-shaped region 8a is formed, of the side wall sheet 6 in an enlarged scale. In the aforementioned corrugations 7, the fiber density is higher at the ridges 7a and the valleys 7b and lower at the side walls 7c. Therefore, the corrugations 7 have cushioning properties. In the band-shaped region 8a (and the band-shaped region 8), the fibers forming the nonwoven fabric 6A are compressed to have a high fiber density. In the band-shaped region 8a, however, the widthwise bending rigidity of the side wall sheet 6 is lower than that of the rigid region where the corrugations 7 are formed.

The density of the higher density portions of the ridges 7a, the valleys 7b and the band-shaped region 8a (and the band-shaped region 8) is preferably at about 0.1 g/cm$^3$.

The array pitch β1, as shown in FIG. 11A, i.e., the pitch of the corrugations 7 is preferably 0.3 to 1.5 mm or more preferably about 0.5 to 1 mm. The contact feel on the skin of the wearer is improved, if the corrugations 7 of the short pitch are formed on the shaping faces. On the other hand, the rising size from the root end 5b to the free end 5c of the leakage preventing side walls 5 is preferably within a range of 5 to 25 mm.

The elastic member 9 to be attached to the free end 5c of the leakage preventing side wall 5 can be made of natural rubber, synthetic rubber, polyurethane or a styrene-butadiene copolymer and can take a shape of string, filament, film, band (or belt) or the like. Alternatively, the elastic member 9 can be cut from a stretchable nonwoven fabric such as an elastic spun-bonded nonwoven fabric or an elastic melt-blown nonwoven fabric.

The paired side wall sheets 6 provided with the elastic member 9 are jointed to the sanitary napkin 1 while being elongated by about 1.2 to 1.8 times.

The support sheet 2 is preferably made of a liquid-impermeable sheet. This support sheet 2 may be exemplified by an air-permeable resin film, a spun-bonded or spun-laced nonwoven fabric made water-repellent, or a nonwoven fabric having an air-permeable resin film bonded to the back face. Here, the support sheet 2 is preferably provided on its back face with both an adhesive layer to be retained on an external wear such as an underwear and a release sheet for protecting the adhesive layer before the sanitary napkin is used.

The liquid-permeable sheet 4 is made of a nonwoven fabric of PE, PP or PET fibers made hydrophilic or their composite fibers, such as a spun-bonded nonwoven fabric or a spun-laced nonwoven fabric. Alternatively, the liquid-permeable sheet 4 is a resin sheet subjected to an opening treatment.

The liquid absorbing layer 3 is made of pulverized pulp or a mixture of pulverized pulp and a highly water-absorbing polymer, and is prepared by enveloping the pulverized pulp or the mixture of the pulverized pulp and the highly water-absorbing polymer by an absorbent sheet such as tissue paper.

FIGS. 4, 5, 6 and 7 show individual modifications of the leakage preventing side walls 5 which are made of the nonwoven fabric 6A.

Figure 4:
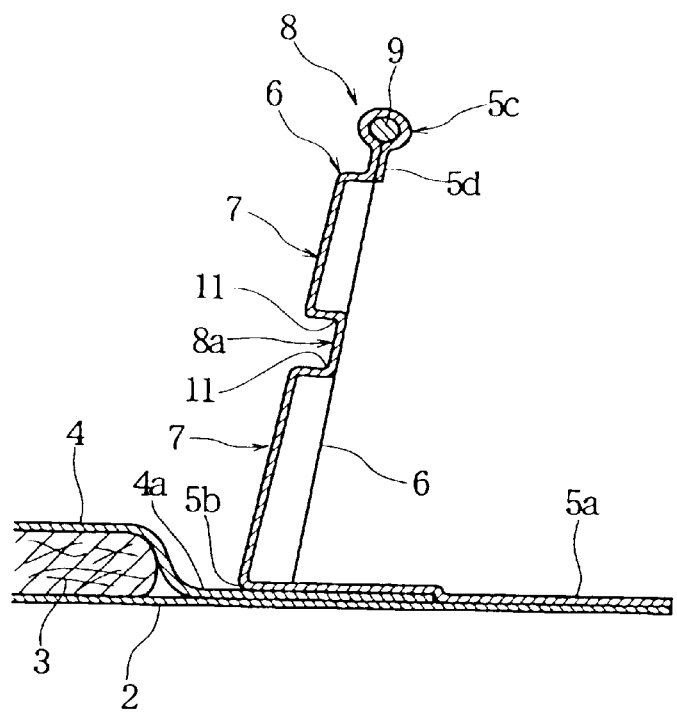
FIG. 4 is a sectional view showing a modification of the sanitary napkin shown in FIG. 2.

In the modification shown in FIG. 4, the side wall sheet 6 made of the nonwoven fabric 6A is raised from the root end portion 5b and is folded back at the free end 5c, but the folded-back terminal 5d is terminated in the vicinity of the free end 5c. Therefore, the leakage preventing side wall 5 is substantially made of only the inner sheet portion of the side wall sheet 6. In this inner sheet portion of the side wall sheet 6, moreover, there are formed the corrugations 7, the band-shaped region 8a and the rigid boundary portions 11.

Here, in the case where the side wall sheet 6 is folded back at the free end 5c so that the leakage preventing side wall 5 is made of the two folded portions (inner and outer sheet portions) of the side wall sheet 6, as shown in FIG. 3, the inner sheet portion (i.e., the folded portion on the lefthand side of FIG. 3) of the side wall sheet 6, as confronting the liquid absorbing layer 3, may exclusively have the corrugations 7 and the band-shaped region 8a, but the outer sheet portion (i.e., the folded portion on the righthand side of FIG. 3) of the side wall sheet 6 may have no corrugation 7 to be substantially flat.

Figure 5:
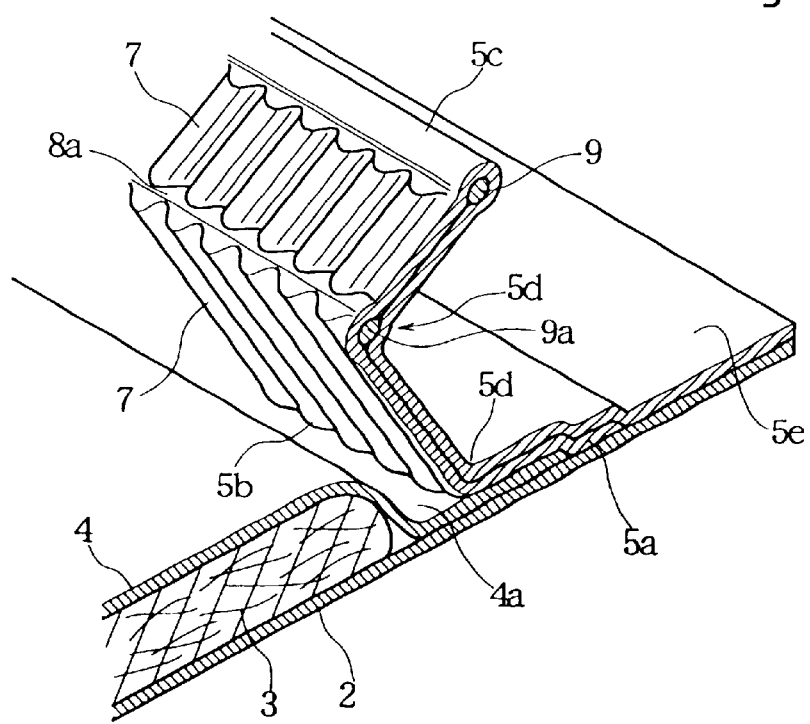
FIG. 5 is a perspective view showing a portion of a modification of the sanitary napkin shown in FIG. 2 and including a section.
Figure 6:
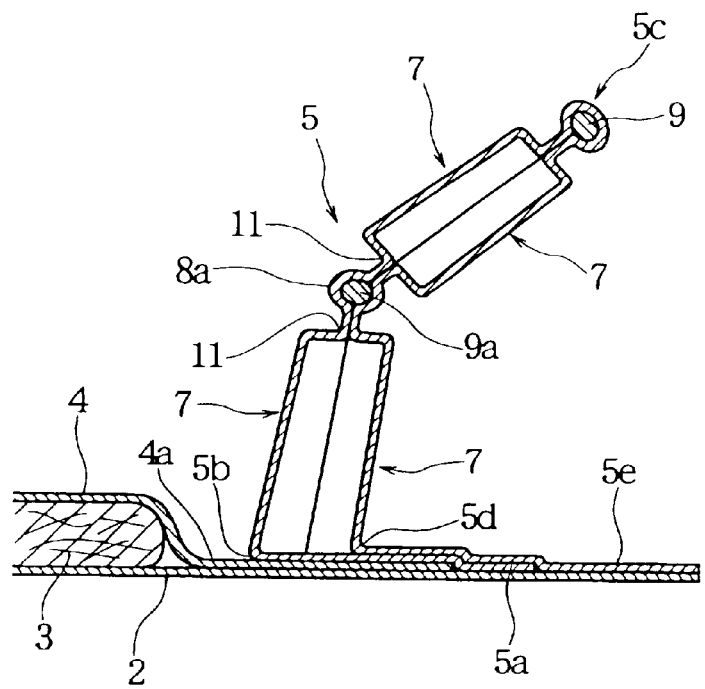
FIG. 6 is a section of the sanitary napkin shown in FIG. 5.

The modification shown in FIG. 5 and sectionally in FIG. 6 is provided with the leakage preventing side walls 5 having a structure similar to that shown in FIG. 3. In this leakage preventing side wall 5, however, another elastic member 9a is disposed in the band-shaped region 8a at the midway portion thereof, in addition to the elastic member 9 disposed at the free end 5c. This elastic member 9a also exhibits the elastic shrinking force in the longitudinal direction (or the direction Y) like the foregoing elastic member 9.

The elastic members 9 and 9a are individually extended to the two longitudinal ends of the sanitary napkin 1 shown in FIG. 1 and are jointed together with the two longitudinal end portions of the leakage preventing side walls 5 to the surface of the liquid receiving side. In the modification shown in FIGS. 5 and 6, therefore, the leakage preventing side walls 5 are given a higher longitudinal tension at the portions having the elastic members 9a so that they are easily folded across the higher tensile portions of the elastic members 9a.

In this case, the shrinking force of the elastic members 9 on the side of the free ends 5c is preferred to be higher than that of the elastic members 9a. By making the shrinking tension of the elastic members 9 higher, the free ends 5c having the elastic members 9 are spaced away from the support sheet 2 on the liquid receiving side by a larger distance than the midway portions having the elastic members 9a. As a result, the leakage preventing side walls 5 can keep the standing positions while bending in the general shape of a letter "L", as shown in FIG. 6.

Figure 7:
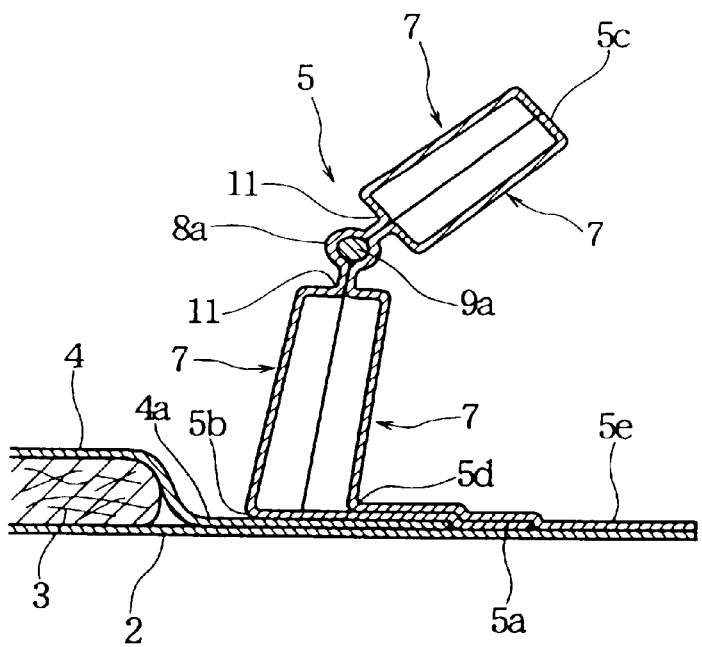
FIG. 7 is a section showing a modification of the sanitary napkin shown in FIG. 2.

In the modification shown in FIG. 7, the side wall sheet 6 is folded back at the free end 5c to form the leakage preventing side wall 5 having the two-layered structure. However, the elastic member 9 is not disposed at the free end 5c, but only the elastic member 9a is disposed at the band-shaped region 8a located at the midway portion of the leakage preventing side wall 5. In this embodiment, the leakage preventing side wall 5 is raised from the liquid receiving side by the elastic shrinking force of the elastic member 9a. However, the portion leading from the elastic member 9a tends to freely deform so that the portion from the elastic member 9a to the free end 5c can fit the skin softly.

Figure 13:
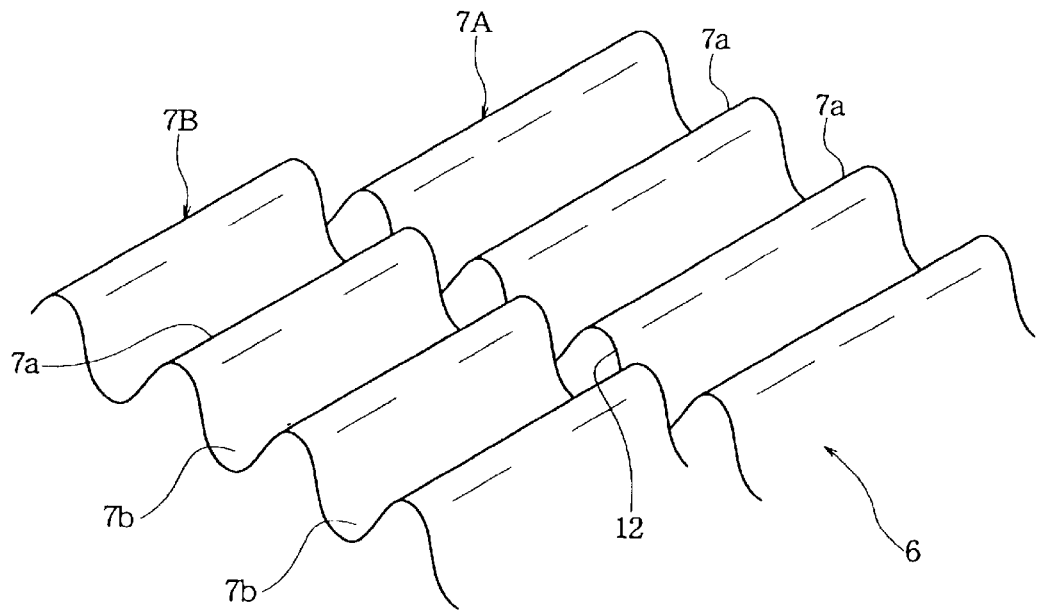
FIG. 13 is a perspective view showing a portion of a second embodiment of the side wall sheet.

FIG. 13 shows a second embodiment of the side wall sheet 6.

In this embodiment shown in FIG. 13, corrugations 7A and corrugations 7B have their wave periods deviated at 12. Specifically, the ridges 7a of the corrugations 7A are substantially synchronized with the valleys 7b of the corrugations 7B. Thus, the corrugations 7A and the corrugations 7B are discontinuous to thereby form a rigid boundary portion 12 extending in the longitudinal direction. In this embodiment, the rigid region having the corrugations 7A and the other rigid region having the corrugations 7B can be folded across the rigid boundary portion 12.

Here in the foregoing embodiments, the single band-shaped region 8a is formed at the midway region between the root ends 5b and 5d and the free end 5c of the leakage preventing side wall 5, but a plurality of band-shaped regions 8a may be formed at the midway region.

The corrugations 7 may be given such a radial pitch away from the root end 5b as is narrower on the side of the root end 5b and wider on the side of the free end 5c of the leakage preventing side wall 5. In this case, the menstrual blood blotted the side wall sheet 6 is collected on the side of the root end 5b as it flows along the corrugations 7 to the root end side so that the menstrual blood having migrated along the leakage preventing side wall 5 is collected and absorbed by the liquid absorbing layer 3.

Here in the foregoing various embodiments shown in FIG. 2 and subsequent Figures, the single side wall sheet 6 is folded back to form the leakage preventing side wall 5. However, the leakage preventing side wall 5 may also be formed of a plurality of side wall sheets individually raised from the root ends, such that two side wall sheets are jointed each other at the free end 5c or at another region to form a jointed portion extending in the longitudinal direction.

Although the description has been made on the embodiments in which the absorbent article of the invention is exemplified by the sanitary napkin, the invention could be applied to a disposable diaper, a urine absorbing pad or another absorbent article.

According to the invention, as has been described in detail hereinbefore, the leakage preventing side walls establish no physical disorder when they come into abutment against the skin, and are easily deformed into a three-dimensional stereoscopic shape along the skin surface of the wearer's body without being irregularly folded. Therefore, an excellent contact between the leakage preventing side walls and the skin can be made to enhance the sideway leakage preventing effect.

Here, 'comprises/comprising' when used in this specification is taken to specify the presence of stated features, integers, steps or components but does not preclude the presence or addition of one or more other features, integers, steps, components or groups thereof.

Although various exemplary embodiments have been shown and described, the invention is not limited to the embodiments shown. Therefore, the scope of the invention is intended to be limited solely by the scope of the claims that follow.

What is claimed is:

1. An absorbent article comprising:
   a main body including a support sheet, a liquid absorbing layer laid on said support sheet, and a liquid-permeable sheet provided on a liquid receiving side of the main body and covering said liquid absorbing layer; and
   leakage preventing side walls provided on two sides of said main body lying opposite one another in a widthwise direction and extending in a longitudinal direction, to have root ends jointed to the surface of said liquid receiving side and to have free ends positioned apart from the surface of said liquid receiving side, wherein each leakage preventing side wall includes: a nonwoven fabric comprising thermoplastic fibers; and two elastic members for exhibiting an elastic shrinking force in the longitudinal direction, wherein said nonwoven fabric is provided with: at least two rigid regions having corrugations, ridges and valleys of which are individually extended in a direction from the root end to the free end of said leakage preventing side wall and are repeated regularly in the longitudinal direction; and a rigid boundary portion in which said corrugations are discontinuous and which is extended in the longitudinal direction midway between the root end and the free end of said leakage preventing side wall;

wherein said two elastic members are respectively attached to said free end and a vicinity of said rigid boundary portion, and wherein the elastic member at said free end has a higher elastic shrinking force than that of the elastic member in the vicinity of said rigid boundary portion.

2. The absorbent article as set forth in claim 1, wherein midway between the root end and the free end of said leakage preventing side wall, there is formed a band-shaped region in which said nonwoven fabric is not corrugated or is corrugated lower than said corrugations and which is extended in the longitudinal direction, and wherein a boundary line between said corrugations and said band-shaped region is said rigid boundary portion.

3. The absorbent article as set forth in claim 1, wherein said leakage preventing side wall has said elastic member attached to said free end.

4. The absorbent article as set forth in claim 1, wherein said leakage preventing side wall has said elastic member attached to the vicinity of said rigid boundary portion but not to said free end.

5. The absorbent article as set forth in claim 1, wherein said leakage preventing side wall is formed such that said leakage preventing side wall possesses at least two sheet portions either by folding a single nonwoven fabric, as extending from said root end, back at said free end to said root end, or by jointing a plurality of nonwoven fabrics, as individually extending from said root end, to one another in the longitudinal direction at said free end or another region, and wherein said rigid regions and said rigid boundary portion are formed within individual sheet portions at identical positions of said leakage preventing side wall.

* * * * *